US011339390B2

(12) United States Patent
Zhang et al.

(10) Patent No.: US 11,339,390 B2
(45) Date of Patent: *May 24, 2022

(54) DNA MICROSCOPY METHODS

(71) Applicants: THE BROAD INSTITUTE, INC., Cambridge, MA (US); MASSACHUSETTS INSTITUTE OF TECHNOLOGY, Cambridge, MA (US)

(72) Inventors: Feng Zhang, Cambridge, MA (US); Joshua Asher Weinstein, Cambridge, MA (US); Aviv Regev, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/554,627

(22) PCT Filed: Sep. 9, 2016

(86) PCT No.: PCT/US2016/051164
§ 371 (c)(1),
(2) Date: Aug. 30, 2017

(87) PCT Pub. No.: WO2017/044893
PCT Pub. Date: Mar. 16, 2017

(65) Prior Publication Data
US 2018/0187183 A1 Jul. 5, 2018

Related U.S. Application Data

(60) Provisional application No. 62/217,639, filed on Sep. 11, 2015.

(51) Int. Cl.
*C12Q 1/6841* (2018.01)
*C12Q 1/686* (2018.01)
*C12N 15/10* (2006.01)
*C40B 40/08* (2006.01)
*G01N 33/50* (2006.01)

(52) U.S. Cl.
CPC ..... *C12N 15/1065* (2013.01); *C12N 15/1096* (2013.01); *C12Q 1/686* (2013.01); *C12Q 1/6841* (2013.01); *C40B 40/08* (2013.01); *G01N 33/5082* (2013.01); *C12Q 2535/122* (2013.01); *C12Q 2537/165* (2013.01); *C12Q 2543/101* (2013.01); *C12Q 2563/179* (2013.01); *C12Q 2565/514* (2013.01); *G01N 33/5023* (2013.01)

(58) Field of Classification Search
CPC ............ C12N 15/1065; C12N 15/1096; C12Q 1/686; C12Q 2535/122; C12Q 2543/101; C12Q 2563/179; C12Q 2565/514; C40B 40/08
See application file for complete search history.

(56) References Cited

U.S. PATENT DOCUMENTS

| | | | |
|---|---|---|---|
| 8,718,351 | B2 | 5/2014 | So et al. |
| 10,655,173 | B2 * | 5/2020 | Zhang .................. C12Q 1/6846 |
| 2012/0003657 | A1 * | 1/2012 | Myllykangas ....... C12Q 1/6869 |
| | | | 435/6.12 |
| 2016/0253584 | A1 * | 9/2016 | Fodor .................. C12Q 1/6813 |
| | | | 235/494 |
| 2016/0265046 | A1 | 9/2016 | Zhang et al. |

FOREIGN PATENT DOCUMENTS

| | | |
|---|---|---|
| WO | 2014047556 A1 | 3/2014 |
| WO | 2015058052 A1 | 4/2015 |
| WO | 2017044893 A1 | 3/2017 |

OTHER PUBLICATIONS

Tan et al. Molecular Beacons. Current Opinion in Chemical Biology 2004; 8: 547-553. (Year: 2004).*
De Vree et al. Targeted sequencing by proximity ligation for comprehensive variant detection and local haplotyping. Nature Biotechnology 2014; 32: 1019-1025 + Online Methods (Year: 2014).*
"International Preliminary Report on Patentability for PCT Application No. PCT/US2016/051164", 1-9.
Dekosky, et al., "High-Throughput Sequencing of the Paired Human Immunoglobulin Heavy and Light Chain Repertoire", Nature Biotechnology, vol. 31, No. 2, Feb. 2013, 166-169.
Glaser, et al., "Puzzle Imaging: Using Large-Scale Dimensionality Reduction Algorithms for Localization", Plos One, Jul. 20, 2015, 23.
Lee, et al., "Highly Multiplexed Subcellular RNA Sequencing In Situ", Science, vol. 343, No. 6177, Mar. 21, 2014, 1360-1363.
Shiroguchi, et al., "Digital RNA Sequencing Minimizes Sequence Dependent Bias and Amplification Noise with Optimized Single-Molecule Barcodes", Proceedings of the National Academy of Sciences, vol. 109, No. 4, Jan. 24, 2012, 1347-1352.
Turchaninova, "Pairing of T-Cell Receptor Chains Via Emulsion PCR", European Journal of Immunology, vol. 43, 2013, 2507-2515.
International Search Report and Written Opinion for International Patent Application No. PCT/US2016/051164, dated Dec. 2, 2016, 14.

* cited by examiner

*Primary Examiner* — Angela M. Bertagna
(74) *Attorney, Agent, or Firm* — Johnson, Marcou, Isaacs & Nix, LLC; F. Brent Nix, Esq.; Rachel D. Rutledge, Esq.

(57) ABSTRACT

The present invention relates to DNA microscopy methods to record the cellular co-localization and/or spatial distributions of arbitrary nucleic acid sequences, or other biomolecules tagged with nucleic sequences. The method involves sequence-components which may identify the targeted sequences-of-interest themselves and/or spatial beacons relative to which their distances are measured.

19 Claims, 11 Drawing Sheets
Specification includes a Sequence Listing.

Part 1: For UMI/UEI of length L, construct L dictionaries

| Example data (L=4) | Dictionary without position 1 | Dictionary without position 2 | Dictionary without position 3 | Dictionary without position 4 |
|---|---|---|---|---|
| UMI/UEI 1: CATT | AAC: 2 | CAC: 2 | CAC: 2 | CAA: 2 |
| UMI/UEI 2: CAAC | ATA: 4 | CTT: 1 | CAT: 1 | CAT: 1 |
| UMI/UEI 3: GGTA | ATT: 1 | GTA: 3, 4 | GAA: 4 | GAT: 4 |
| UMI/UEI 4: GATA | GTA: 3 | | GGA: 3 | GGT: 3 |

Part 2: Loop through all dictionaries, assign all sequences related by any out of the L dictionaries UMI/UEI 1: None
UMI/UEI 2: None
UMI/UEI 3: (4)
UMI/UEI 4: (3)

FIG. 7

GFP (target)
RFP (target)
GAPDH (target)
ACTB (beacon)

3e5 transcripts mapped
7e6 reads sequenced

DNA MICROSCOPY METHODS

CROSS-REFERENCE TO RELATED APPLICATIONS

This application is a National Stage application of International Application No. PCT/US2016/051164 filed Sep. 9, 2016, which claims the benefit of U.S. Provisional Application No. 62/217,639 filed Sep. 11, 2015. The entire contents of the above-identified applications are hereby fully incorporated herein by reference.

The foregoing applications, and all documents cited therein or during their prosecution ("appln cited documents") and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under Grant Nos. MH100706 and HG009276 awarded by the National Institutes of Health. The government has certain rights in the invention.

FIELD OF THE INVENTION

The present invention relates to DNA microscopy methods, in particular recording spatial distributions of DNA or RNA, or molecular targets tagged with DNA or RNA, in cells or biological tissue at cell-population, single-cell, or subcellular resolution by randomized barcoding of DNA or cDNA before and during in situ amplification.

SEQUENCE LISTING

The contents of the substitute electronic sequence listing (BROD_0750US_ST25.txt"; Size is 7,627 bytes) was created on Jul. 23, 2020) is herein incorporated by reference in its entirety and replaces any and all previously submitted Sequence Listings.

BACKGROUND OF THE INVENTION

Cellular phenotype is commonly characterized by mRNA expression profiling. However, in heterogeneous populations of cells, profiling cell populations in bulk discards all information pertaining to the associations of specific mRNA transcripts in individual cells. In immunoglobulin-producing lymphocytes, for example, pooled sequencing results in the separate characterizations of immunoglobulin heavy- and light-chains, peptides whose co-expression within a cell determines an immunoglobulin's antigen-specificity. To resolve this, heavy- and light-chain mRNA produced by individual lymphocytes may be made to associate in the sequence of a polymerase chain reaction (PCR) product (Embleton M J, et al. Nucleic Acids Res. 1992 Aug. 11; 20(15): 3831-3837). In this method, cells from two clonal populations were fixed and permeabilized, their heavy- and light-chain mRNA reverse transcribed to cDNA, and the cDNA amplified by PCR with primers containing reverse-complementary overhangs which allowed heavy- and light-chain PCR product to concatenate during the reaction. The fidelity of chimeric heavy/light chain PCR product to the original intracellular co-localization could then be verified either using fluorescent primers using fluorescence microscopy or by screening of bacterial colonies transfected with chimeric PCR product. (Embleton M J, et al. Nucleic Acids Res. 1992 Aug. 11; 20(15): 3831-3837).

High-throughput sequencing can identify large numbers of heavy- and light-chain variable regions ($V_H$ and $V_L$) in a given B-cell repertoire, but information about endogenous pairing of heavy and light chains is lost after bulk lysis of B-cell populations. A way to retain this pairing information involves depositing single B cells ($>5 \times 10^4$ capacity per experiment) in a high-density microwell plate (125 pl/well) and lysing (DeKosky B J, et al. Nat Biotechnol. 2013 February; 31(2):166-9). mRNA is then captured on magnetic beads, reverse transcribed and amplified by emulsion $V_H:V_L$ linkage PCR and the linked transcripts are analyzed by Illumina high-throughput sequencing (DeKosky B J, et al. Nat Biotechnol. 2013 February; 31(2):166-9).

RNA sequencing (RNA-Seq) is a powerful tool for transcriptome profiling, but is hampered by sequence-dependent bias and inaccuracy at low copy numbers intrinsic to exponential PCR amplification. To mitigate these complications to allow truly digital RNA-Seq, a large set of barcode sequences is added in excess, and nearly every cDNA molecule is uniquely labeled by random attachment of barcode sequences to both ends (Shiroguchi K, et al. Proc Natl Acad Sci USA. 2012 Jan. 24; 109(4):1347-52). After PCR, paired-end deep sequencing is applied to read the two barcodes and cDNA sequences. Rather than counting the number of reads, RNA abundance is measured based on the number of unique barcode sequences observed for a given cDNA sequence (Shiroguchi K, et al. Proc Natl Acad Sci USA. 2012 Jan. 24; 109(4):1347-52). The barcodes may be optimized to be unambiguously identifiable, even in the presence of multiple sequencing errors. This method allows counting with single-copy resolution despite sequence-dependent bias and PCR-amplification noise, and is analogous to digital PCR but amendable to quantifying a whole transcriptome (Shiroguchi K, et al. Proc Natl Acad Sci USA. 2012 Jan. 24; 109(4):1347-52).

Prior technologies, such as those described above, to identify the contents of individual cells required their dissociation so that they may be analyzed individually. In the case of structurally fragile cell types, such as neurons, this generally required severing whole cell parts, such as dendrites that branch from the main cell body.

Fluorescence in situ sequencing, or FISSEQ, is a method that allows the acquisition of mRNA/cDNA sequences directly from within cell monolayers or fixed tissue (Lee J H et al. Science. 2014 Mar. 21; 343(6177):1360-3). mRNA transcripts are reverse-transcribed into cDNA and fixed to the cellular matrix. mRNA is degraded, and the cDNA subsequently circularized so that polonies comprising long repeats of cDNA sequence may be formed by rolling circle amplification (RCA). SOLiD sequencing (sequencing by oligonucleotide ligation and detection) is then used to read out 30 bp reads that allow comparison with reference gene transcripts. In order to resolve individual transcripts, signals are suppressed so that polonies are sufficiently sparse to be distinguished from one another optically. FISSEQ requires high-quality optics for each sample to be analyzed. Moreover, because of trade-offs between a microscope's depthof-field and its imaging resolution, samples must be properly arranged on a two-dimensional plane to be analyzed.

Citation or identification of any document in this application is not an admission that such document is available as prior art to the present invention.

SUMMARY OF THE INVENTION

The invention solves the challenge of sequencing DNA or RNA, or identifying molecular targets tagged with DNA or RNA, in non-dissociated fixed cells or sectioned or intact biological tissue at single-cell or subcellular resolution.

The present invention relates to randomized barcoding of nucleic acids before and during in situ amplification. Random barcoding of nucleic acids before in situ amplification creates a UMI (unique molecular identifier) for nucleic acid template molecules. Concatenation of nucleic acid-amplification products is accompanied by random-barcoding of concatenation events, generating unique event identifier's, or UEI's. Sequencing UMI's and UEI's and combining them generates a hierarchy of physical co-localization among groups of template nucleic acid molecules in the biological sample.

Advantages of the present invention is that (a) DNA microscopy may work with a single sample, and this sample may be non-canonical and idiosyncratic (such as, but not limited to, tumor tissue, lymphatic tissue or neural tissue); (b) image-capture is volumetric with no sectioning required; (c) the protocol stands alone and does not require specialized equipment; (d) the protocol uses commercialized DNA sequencers to provide high coverage of single template molecules, thereby enabling single-base resolution, low error rates, and high read lengths of gene sequences of interest.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 7 illustrates UMI/UEI local-similarity hashing alignment in advance of EASL clustering. Sequences (which may correspond to either a library of UMI's or UEI's) are first grouped by perfect identity. In Part 1, for sequences of full length L, L separate dictionaries are generated. In dictionary i, all sequences—each having had position i removed—are catalogued. In Part 2, all dictionaries are looped through, and all sequence associations that are found and recorded in a final list.

DETAILED DESCRIPTION OF THE INVENTION

Figure 1:
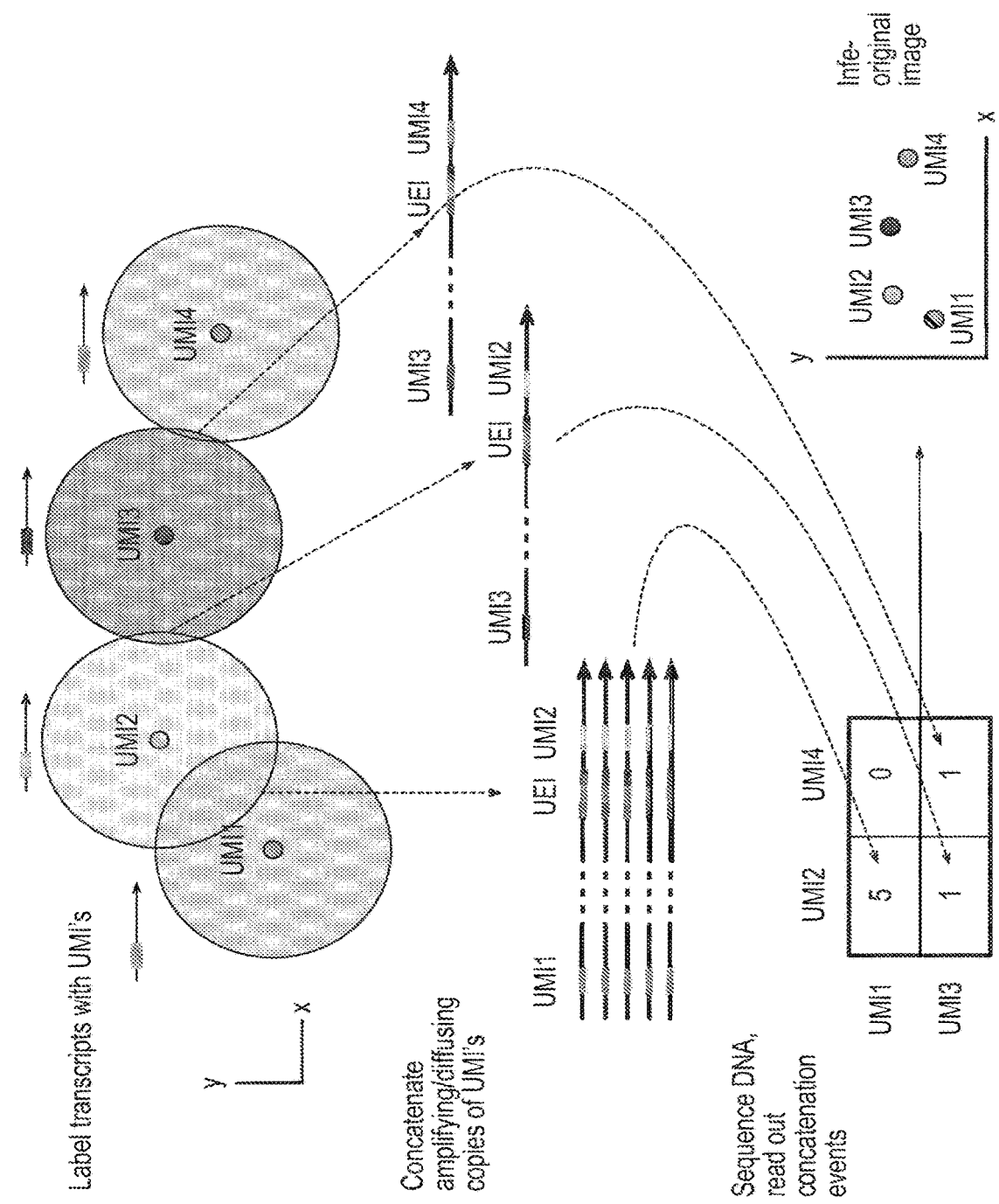
FIG. 1 depicts a simplified bird's-eye view of the invention.
Figure 2:
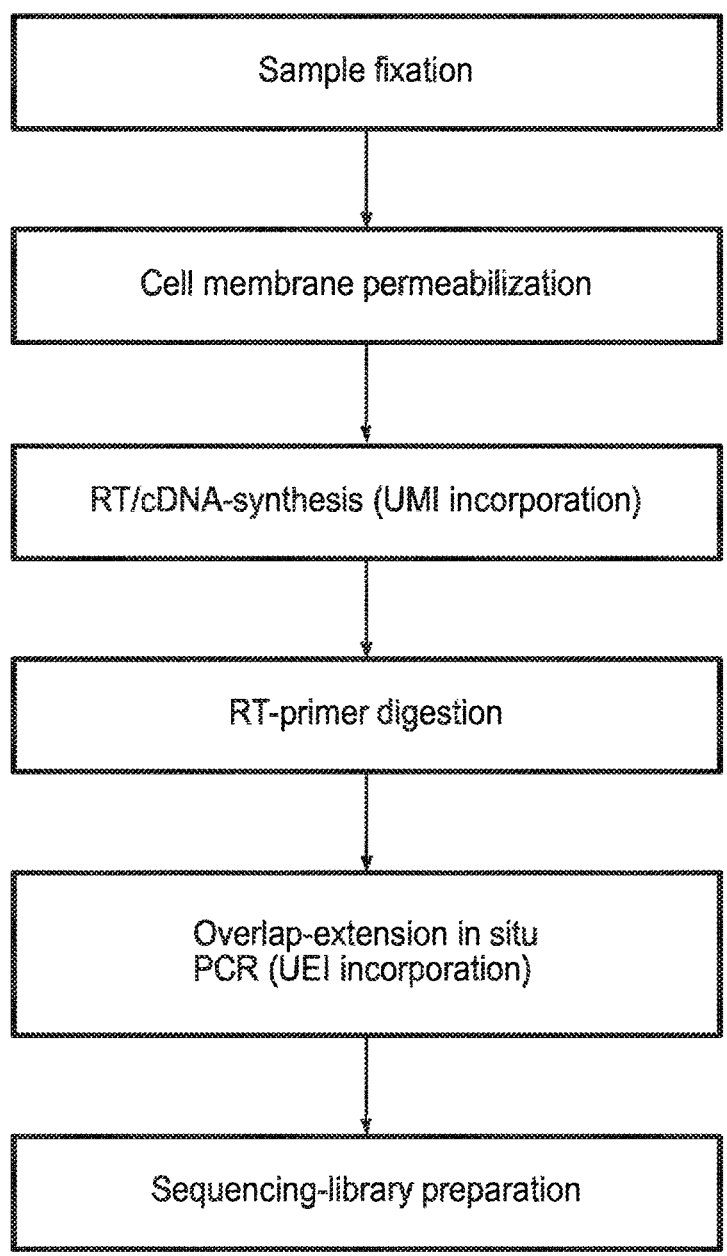
FIG. 2 provides a flowchart of the method's experimental structure. Following sample fixation and membrane permeabilization, RNA is denatured (chemically under acid-treatment and/or by heating). Reverse transcription (cDNA synthesis) incorporates primers with randomized UMI nucleotides flanked by reverse-adapters (see FIGS. 3 and 4 for further detail). Residual primers from reverse transcription are degraded using a combination of enzymatic digestion (such as with Exonuclease I) and washing. Overlap-extension in situ PCR concatenates UMI-labeled amplicons together, and incorporates randomized UEI nucleotides between them. Reaction products are then prepared as libraries for NGS (Next Generation Sequencing).

Embodiments disclosed herein are directed to DNA microscopy, a technology that efficiently generates DNA-sequence read-outs of tissue microstructure. In certain embodiments this is achieved by encoding into DNA the cellular co-localization and/or spatial distributions of arbitrary DNA/RNA sequences, or other biomolecules tagged with DNA/RNA sequences. Biomolecules are first tagged with randomized DNA or RNA sequences, called UMI's (unique molecular identifiers). These tags, which may incorporate the sequence of a targeted gene sequence, are amplified by PCR in situ with oligonucleotide primers. These primers both direct the concatenation of PCR products, retaining their original UMI tags, as well as insert UEI's (unique event identifiers) to label each concatenation event uniquely. Because UMI-tagged PCR products must diffuse in order to concatenate, the UEI frequency between any two UMI's is a function of the distance between the original UMI tags from which they were copied. By precisely quantifying concatenation frequencies using high-throughput DNA sequencing, biomolecules identities, abundances, positions, and local tissue densities may therefore be inferred. DNA microscopy thereby allows DNA molecules it generates to encode the physical forms (i.e. the image) of the specimens from which they originate. A general overview of the present invention, as it relates to mapping images of gene transcripts, is presented in FIG. 1.

DNA microscopy may be interchangeably referred to as molecular microscopy or volumetric imaging by proximal unique molecular identifiers ("UMI") reaction ("VIPUR") microscopy.

As used herein, a unique molecular identifier (UMI) is a randomized DNA sequence serving as a unique molecular identifier.

As used herein, a unique event identifier (UEI) is a randomized DNA sequence serving as a unique molecular identifier generally involved in overlap-extension.

The terms of UMI and α-UID may be used interchangeably.

The terms of UEI and β-UID may be used interchangeably.

The bulk of the experimental phase of DNA microscopy can be broken down into 3 distinct stages.

The first stage is UMI generation. During this stage, unique molecular identifiers—which may be referred to as UMI's—label individual template molecules using at least 10 randomized bases. This subsumes the in situ preparation, reverse transcription, and the disposal of residual reagents from each of these steps. Importantly, this disposal includes the use of multiple washes and Exonuclease I digestion, which rids the sample of free remaining single-stranded oligonucleotides (cDNA is protected by its duplexing with mRNA).

The second stage is UEI generation. During this stage, in situ PCR is run with overlap-extension adapters attached to the 5' end of two universal primers. Overlap-extension occurs between those transcripts that have been reverse-transcribed as "beacons" and those transcripts that have been reverse-transcribed as "targets". Overlap-extension incorporates at least 10 random bases in between the two amplicons, and thereafter, as these concatemers are copied by further amplification, so too are these at least 10 bases.

The third stage is NGS library preparation. During this stage, in situ PCR products are extracted and amplified in such a way that they may be easily sequenced. A key part of this stage is preventing further formation of concatemers. To this end, this protocol makes use of "interference oligonucleotides" with 3'-phosphate caps [Turchaninova et al., Pairing of t-cell receptor chains via emulsion per. Eur J Immunol, 43(9):2507-2515, September 2013].

The present invention relates to the scalable analysis of DNA sequencing products from the DNA microscopy amplification reaction. The scalable analysis involves two challenges, one being UMI/UEI error correction, the second being UMI position inference.

UMI/UEI error correction involves sequence-clustering of N UMI or UEI sequences, where N is large. If comparisons of these N sequences were computed directly, this would require $N^2$ comparisons. A solution involves (1) reducing error correction to a clustering problem requiring only knowledge of nearest neighbors and (2) performing local similarity hashing to align UMI/UEI sequences to each other.

UMI position inference involves searching for an optimal positioning of N UMI's: a relative positioning problem that would similarly require $N^2$ comparisons per iteration of the optimization algorithm if this were computed directly. In one example embodiment, optimization involves using the Barnes-Hut algorithm [A hierarchical o (n log n) force-calculation algorithm. Nature, 324:446{449, December 1986] for reducing the $N^2$ comparisons to N log N comparisons. In another example embodiment, optimization comprises using the Fast Gauss Transform for reducing $N^2$ comparisons to N comparisons. (Greengard and Strain. The Fast Gauss Transform, SIAM Journal on Scientific and Statistical Computing, 1991).

Figure 10:
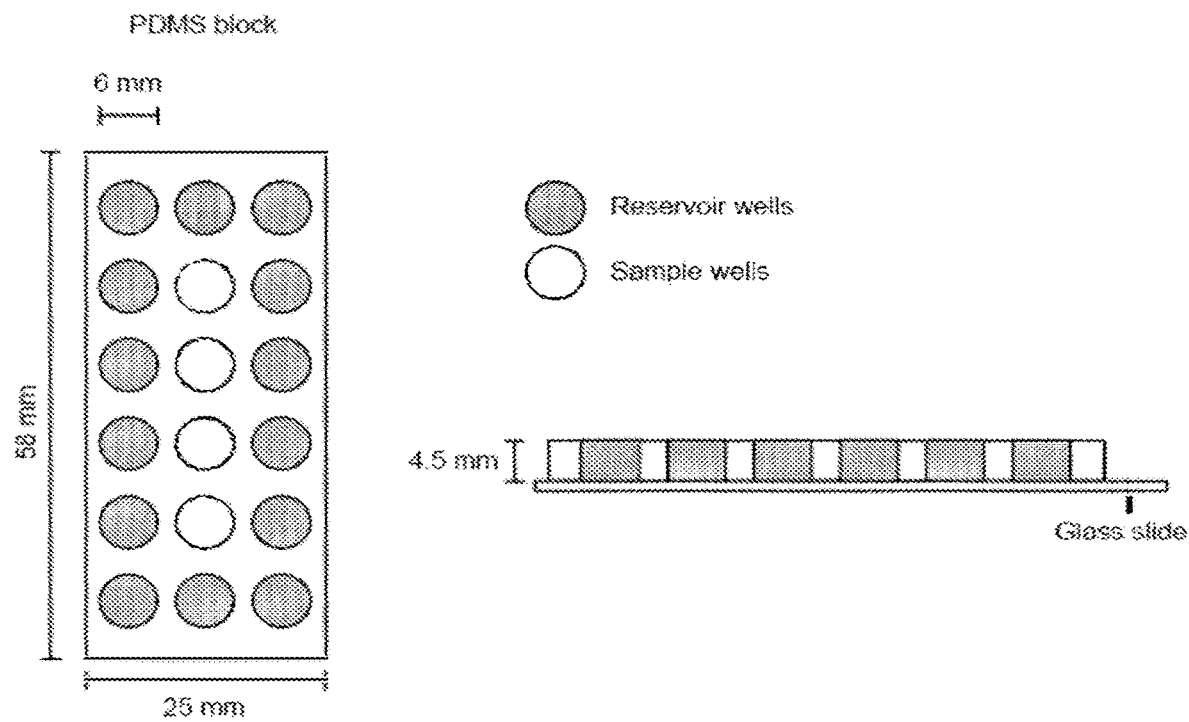
FIG. 10 depicts one embodiment of reaction chamber preparation, which enables cell/tissue adhesion, sample imaging, and the DNA microscopy reaction.
Figure 11:
FIG. 11 depicts inferred positions of transcript sequences from a Beacon-Target DNA microscopy experiment. Each dot corresponds to a UMI, and its color corresponds to the amplicon to which read-out sequence matches.

In preparation for the experiment, reaction chambers are designed in order to maximally adhere cells while providing a thermally robust container for PCR thermocycling. For the former criterion, (3-aminopropyl)triethoxysilane, or APTES (Sigma 440140), may be used to preliminarily silanize a glass surface, such as a 2% acetone solution [Bagasra O. Protocols for the in situ PCR amplification and detection of mRNA and DNA sequences. Nat Protoc., 2(11):2782-2795, 2007], thereby coating it with covalently-linked, positively charged functional groups. In one embodiment, uncured PDMS is poured into petri dishes to a height of approximately 4.5 mm. PDMS is cured, and 6 mm diameter holes are punched in a regular pattern and in sufficient number so that holes to be used as fluid reservoirs completely surround wells to be used for samples. PDMS is then plasma-bonded to uncoated white glass slides (FIG. 10). Glass chambers are subsequently silanized. In another embodiment silanized glass beads are anchored into PCR-plate wells containing about 25 µl of uncured PDMS. The plates are spun down and cured, such that the PDMS functions as an inert hydrophobic "glue". The tops of the silanized glass beads are then exposed for cell adhesion.

The following cell plating protocol may be followed. PDMS-embedded silanized glass beads or PDMS-bonded and silanized glass slides are assembled and UV sterilized under a laminar flow hood for 30 minutes. After washing once with 1×PBS, a 1:100 dilution of fibronectin (Sigma F1141) in PBS is added at a volume of 40 µl on top of the beads or 60 µl on top of slides and incubated for 1 hour at room temperature. Immediately after removing BT-549 expressing RFP (Cell Biolabs AKR-255) and the human cell line MDA-MB-231 expressing EGFP (Cell Biolabs AKR-211) may be plated in each. The cells may then be co-cultured for 36 hours.

After culturing, growth medium is removed and cells are washed once with 1×PBS. Initial pre-reverse transcription treatments may follow Lee et al. [Highly multiplexed subcellular RNA sequencing in situ. Science, 343(6177): 1360-1363, March 2014]. Cells are fixed in 4% formaldehyde (Sigma F8775) in 1×PBS for 15 minutes at room temperature. Formaldehyde is aspirated and replaced by 3×PBS, and left for 10 minutes. Samples are washed twice for 10 minutes in 1×PBS, and then permeablized with a solution of 0.25% TRITON X-100 (Sigma 93443) in 1×PBS for 15 minutes. Samples are then aspirated, washed twice with 1×PBS, and then treated with 0.1 N HCl for 2 minutes and washed an additional three times in 1×PBS.

In the following portion of the protocol, primer-names are used in reference to TABLE 2.

Reverse transcription is performed with "target" primers (5)-(2)-(4)-GAPDH, (5)-(2)(4)-GAPDH, and (5)-(2)-(4)-GAPDH and a "beacon" primer (3)-(2)-(1)-ACTB all added to 850 nM each, in a reaction containing dNTP (400 Superase-In (1 U/µl, Life Technologies AM2696), DTT (4 mM), 1× First-Strand Buffer, and SUPERSCRIPT III (10 U/µl, Life Technologies 18080-044). Reverse transcription is performed by incubating at 60° C. for 3 minutes, followed by 42° C. for 60 minutes. Samples are subsequently kept on ice, until washed twice with 1×PBS, followed by an additional wash with water. Immediately afterward, Exonuclease I digestion is performed in a reaction containing 1× Exonuclease I buffer (NEB B0293S) and 1.4 U/µl Exonuclease I (NEB M0293L), incubated for 40 minutes at 37° C. Samples are then washed three times in 1×PBS for 1 minute each, and left at 4° C. until addition of in situ PCR-mixes.

In situ PCR reaction-mixes may be prepared as follows. HPLC-purified overlap-extension primers with acrydite-modified 5' ends (10')-(2)-(9) and (10)-(2)-(3) are added to final concentrations of 400 nM each, the primers (5) and (8) are added to final concentrations of 300 nM each, and the second-strand synthesis primers (9sh)-(7(−))-GAPDH, (9sh)-(7(−))-GFP, (9sh)(7(−))-RFP, and (8sh)-(6(−))-ACTB are added to final concentrations of 30 nM each. The reaction further contains dNTP (200 nM), MgCl2 (1.6 mM), 40.8 mg/ml 2-arm thiolated PEG (Laysan Bio SH-PEG-SH-3400-1GR), 55 mg/ml 4-arm acrylated PEG (Laysan Bio PEG-ACRL-10K1GR), 1×PCR buffer (without magnesium), 0.5 ug/ul BSA, 8% glycerol, and 1:250 dilution Platinum Taq DNA polymerase (Life Technologies 10966018). The reaction solution is mixed by pipetting, ensuring no bubbles, and a hydrogel left to form for 35 minutes at room temperature. Afterward thermocycling is performed as follows: 95° C. 2 min, 10×(95° C. 30 s, 68° C. 1 min), 2×(95° C. 30 s, 55° C. 30 s, 68° C. 1 min), 16×(95° C. 30 s, 60° C. 30 s, 68° C. 1 min), 68° C. 1 min, 4° C. Reactions are transferred on ice to −20° C., where they can be stored until NGS library preparation.

Samples may be thawed on ice, and hydrogel dissolution may be performed by adding 1 part dissolving-reagent (460 mM KOH, 100 mM EDTA, 42 mM DTT) per 5 parts hydrogel. Samples may be left to incubate at 4° C. for 2 hours for the reagent to diffuse in, after which it may be heated to 72° C. for 5 minutes, and then cooled back down. Stop solution (made by adding 400 µl 1 M HCl to 600 µl 1 M Tris-HCl pH 7.5) may be added in the equivalent volume as the dissolving-reagent, and samples may be immediately mixed by pipetting.

Proteinase-K mix may be prepared as 0.36% TWEEN-20 and 360 µg/ml proteinase K (Sigma P4850) in 10 mM Tris-HCl pH 8. 4 parts of proteinase-k mix may be added per 10 parts neutralized sample and then mixed by pipetting. Samples may be incubated at 50° C. for 25 minutes, and then transferred to ice. Samples may be diluted 1:2 in 10 mM Tris-HCl pH 8, mixed by pipetting, and transferred to a new set of wells, where they may be purified by the AMPURE XP protocol, using an addition of 0.65 volumes of AMPURE XP beads. Samples may be eluted into 35 µl 10 mM Tris-HCl pH 8.

Interference oligonucleotide-mix [Turchaninova et al., Pairing of t-cell receptor chains via emulsion per. Eur J Immunol, 43(9):2507-2515, September 2013] consisting of the oligos 10T-OEc-P: TTTTTTTTTTATTCC-CATGGCGCGCCA/3Phos/(SEQ ID NO: 15) and 10T-OE-P: TTTTTTTTTTGGCGCGCCATGGGAATAA/3Phos/ (SEQ ID NO: 16) at final concentrations of 50 µM each may be prepared in advance. Re-amplification may be performed by adding (in 15 µl sample+15 µl master-mix reactions) interference oligonucleotides to final concentrations of 3.2 µM each, the primers CCCACTTCTCTCGACGCTCTTCCGATCT (SEQ ID NO: 17) and (12)-(5) to final concentrations of 300 nM each, MgSO4 to final concentration 1.5 mM, dNTP to final concentration 0.2 mM, 1×HiFi PCR buffer (without magnesium), and 1:250 dilution Platinum Taq HiFi (Life Technologies 11304-011). Reactions may be thermocycled 95° C. 2 min, 20×(95° C. 30 s, 68° C. 2 min), and then stored at 4° C. Later, samples may be purified by the AMPURE XP protocol, using an addition of 0.65 volumes of AMPURE XP beads.

A final last-stage amplification may be performed with primers (1'(long)) and (12)-(5) and at final concentrations of 300 nM each, MgSO4 to final concentration 2 mM, dNTP to final concentration 0.2 mM, 1×HiFi PCR buffer (without magnesium), and 1:250 dilution Platinum Taq HiFi (Life Technologies 11304-011). Reactions may be thermocycled 95° C. 2 min, 5×(95° C. 30 s, 58° C. 30 s, 68° C. 2 min), 5×(95° C. 30 s, 68° C. 2 min), 68° C. 5 min, 4° C.

Figure 3:
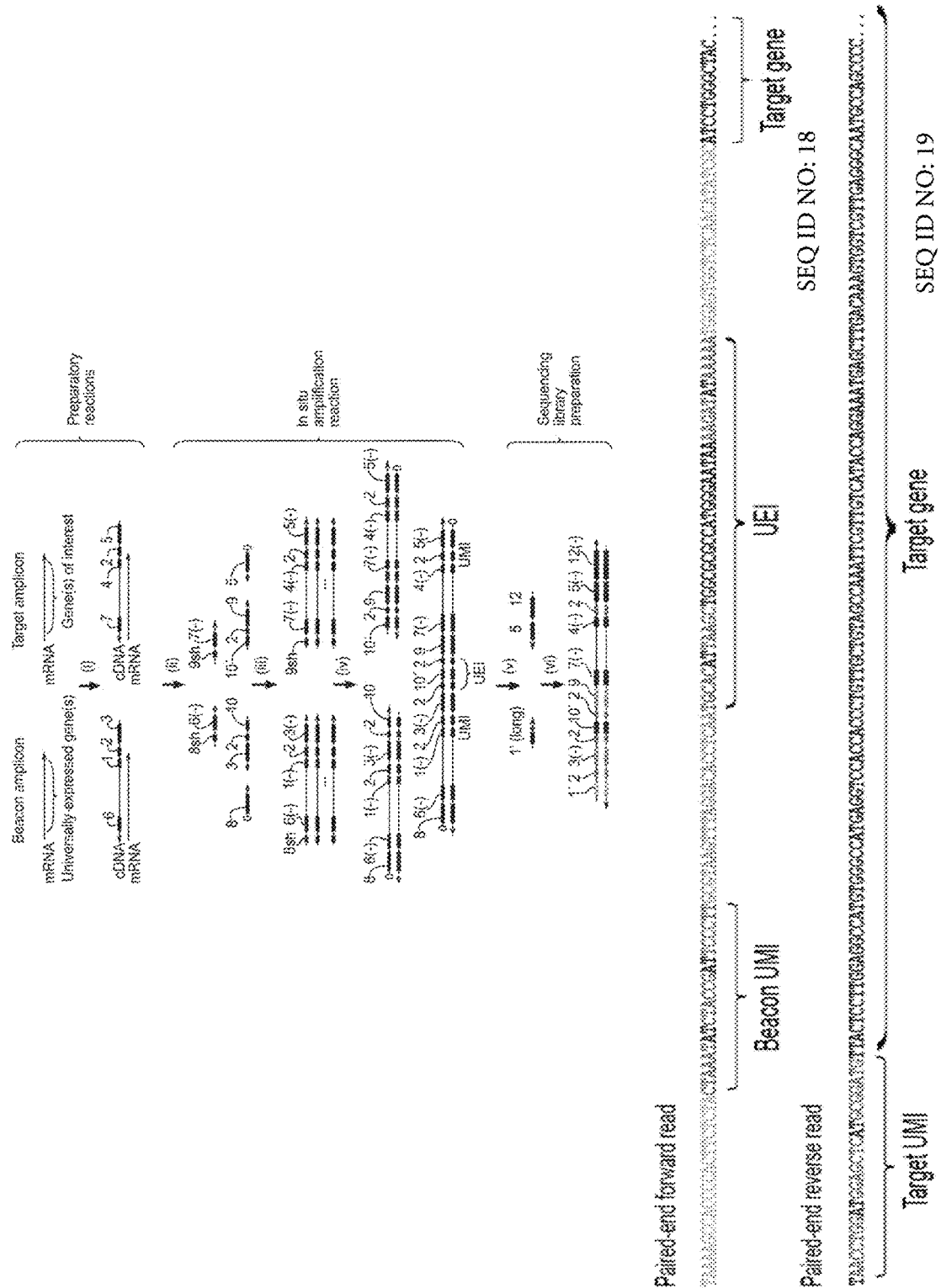
FIG. 3 illustrates a Beacon-Target embodiment of the DNA Microscopy experimental flow for gene-specific amplification. Following cell fixation and permeabilization (i), cDNA synthesis proceeds for beacon-transcripts with primers containing a beacon-specific sequence (1), a randomized UMI sequence (2), and a universal handle (3). The cDNA product extends to include a new beacon-specific priming site (6). cDNA from target-transcripts is synthesized with primers containing a target-specific sequence (4), a randomized UMI sequence (2), and a universal handle (5), with the product containing a new target-specific priming site (7). Following exonuclease I treatment (ii), the in situ overlap-extension PCR reaction is prepared. Second-strand synthesis primers specific to priming sites (6) and (7) are added at a low concentration. These primers contain, on their 5'-ends, short universal handles (8sh) and (9sh) with low melting temperatures. PCR primers include a primer containing the universal handle (8) subsuming the short handle (8sh) and a primer containing the universal handle (9) subsuming the short handle (9sh), the latter containing on its 5' end an overlap-extension adapter sequence (10') and randomized nucleotides (2). PCR primers further include a primer containing the universal handle (5) and a primer containing the universal handle (3) in addition to randomized nucleotides (2) and the overlap-extension adapter sequence (10), reverse-complementary to (10'), on its 5' end. Initially, DNA amplification (iii) proceeds by thermocycling with a high primer-annealing temperature above the maximum for priming the short sequences (8sh) and (9sh). This results in a linear (i.e. constant) amplification rate of both beacon and target amplicons. Subsequently, primer-annealing temperatures are lowered so that (8sh) and (9sh) may be primed, resulting in exponential amplification (iv). The reaction results in overlap-extension between amplicon molecules, leading to both the monomeric and dimeric/concatemer products shown. In these products, UMI's retain information on template molecules of origin, and newly incorporated randomized nucleotides comprise UEI's that label unique cross-linking (i.e. overlap-extension) events. After reaction product elution (v), sequencing library preparations are prepared by amplifying from universal handles (1) and (5) to incorporate NGS adapters (vi). During this reaction, overlap-extension suppression is performed using the techniques listed in TABLE 1, individually or in combination. Example forward- and reverse-reads from the final NGS product are shown. The sequencing is then analyzed (FIG. 5).
Figure 4:
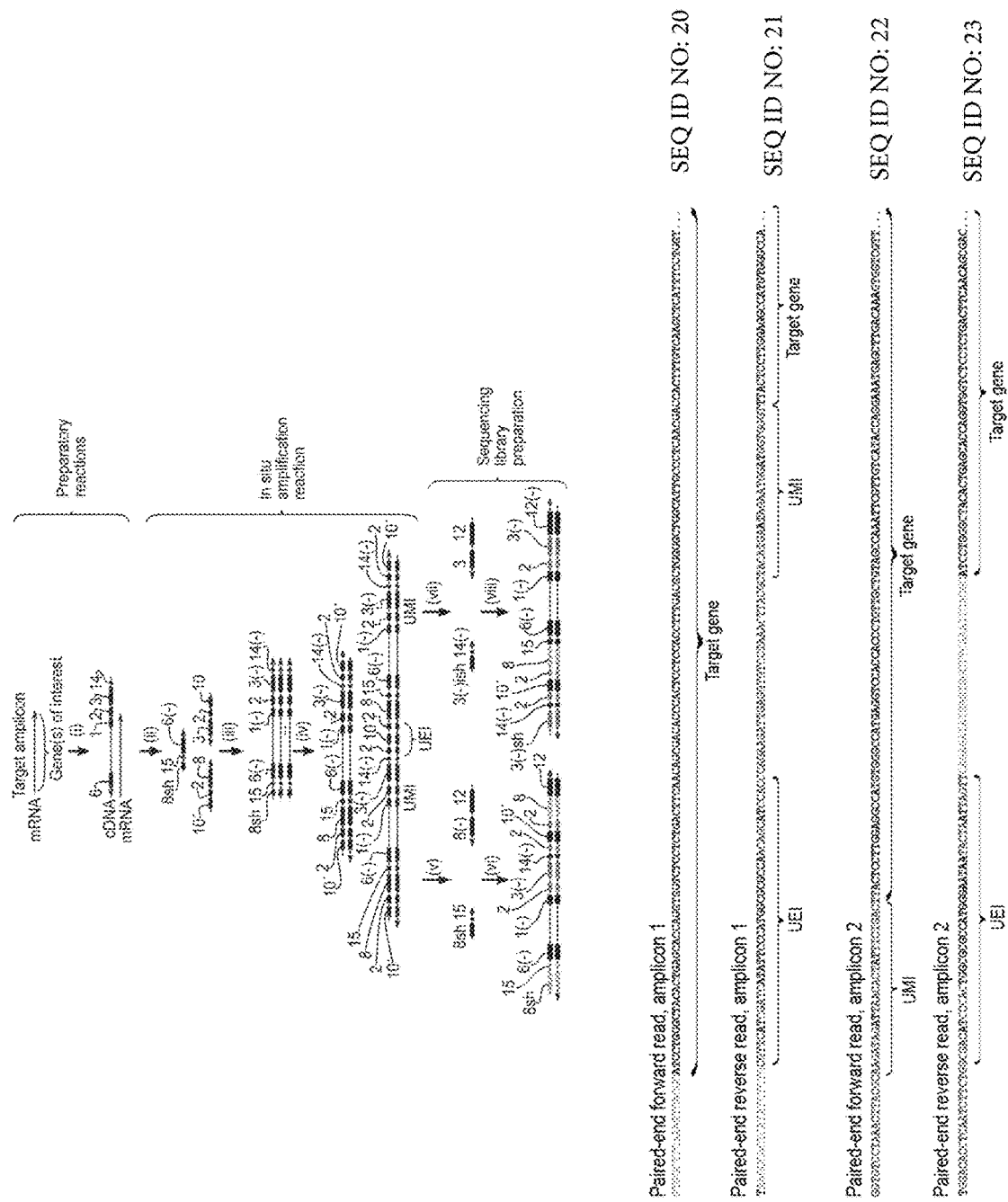
FIG. 4 illustrates a Target-Target embodiment of DNA microscopy. Here, cross-linked products comprise repeats of the same structural unit. Target-Target molecular microscopy follows the same experimental flow as Beacon-Target Molecular Microscopy, except that beacon gene transcripts are not amplified by their own primer sets (meaning that all amplified products are treated identically), permitting a UMI's concatenation both to other UMI's as well as to itself. Two small sequences, (14) and (15), are inserted into reverse-transcription and second-strand synthesis primers, respectively, and these permit separate amplification of the two overlapping sides of the final cross-linked amplicon products (vi and viii). During library preparation, because both sides of the amplicon are identical, interference-oligo technique (TABLE 1, Turchaninova M A et al. Eur J Immunol. 2013 September; 43(9):2507-15) may be used to suppress late-stage overlap-extension. The two amplification reactions are compared and matched based on shared UEI sequences (FIG. 6).
Figure 5:
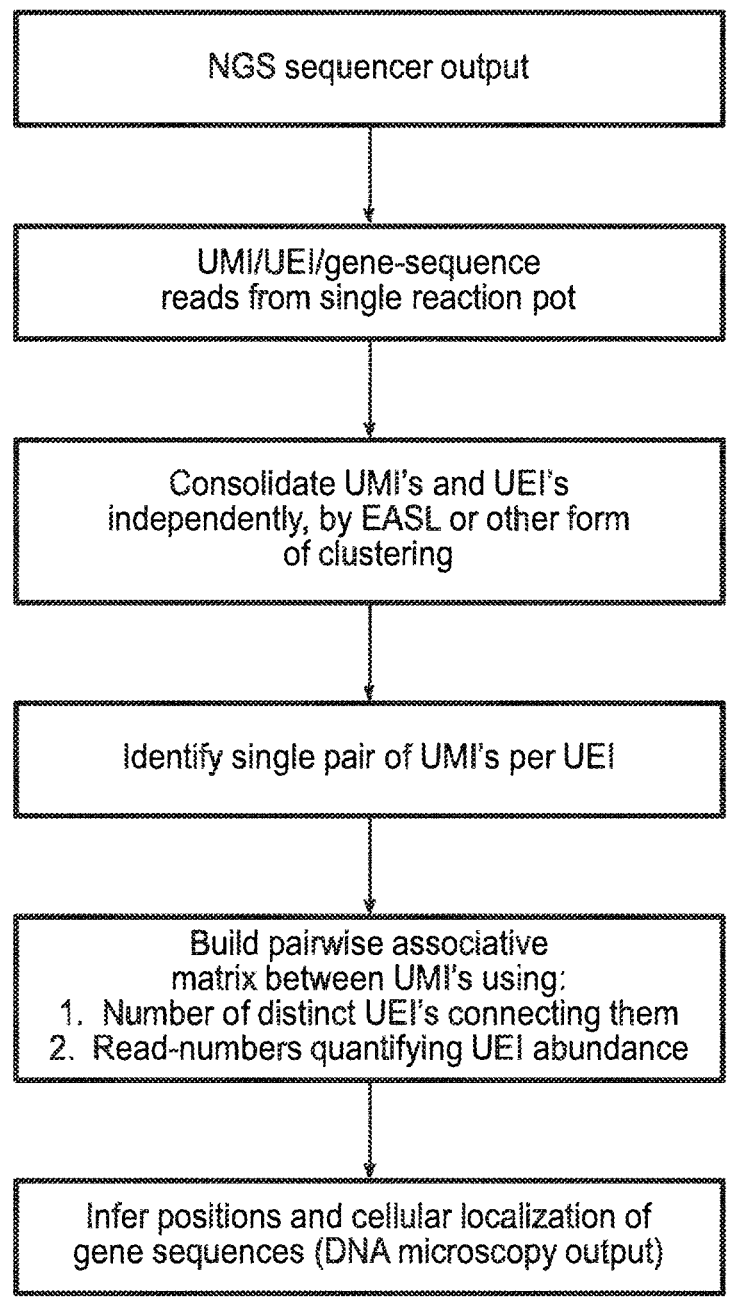
FIG. 5 illustrates the data-flow from Next Generation Sequence output for Beacon-Target DNA Microscopy.
Figure 6:
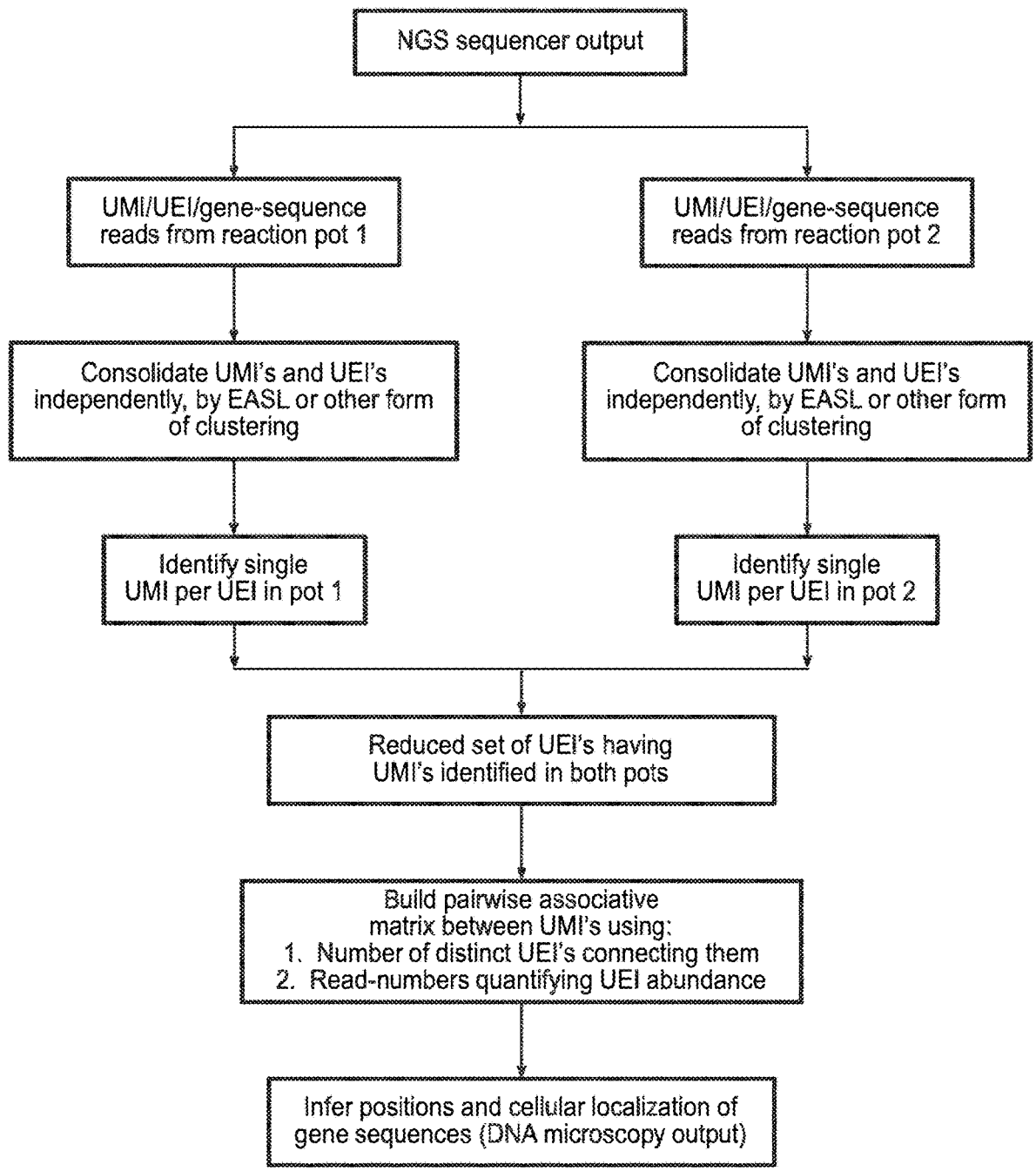
FIG. 6 illustrates the data-flow from Next Generation Sequence output for Target-Target DNA Microscopy.
Figure 8:
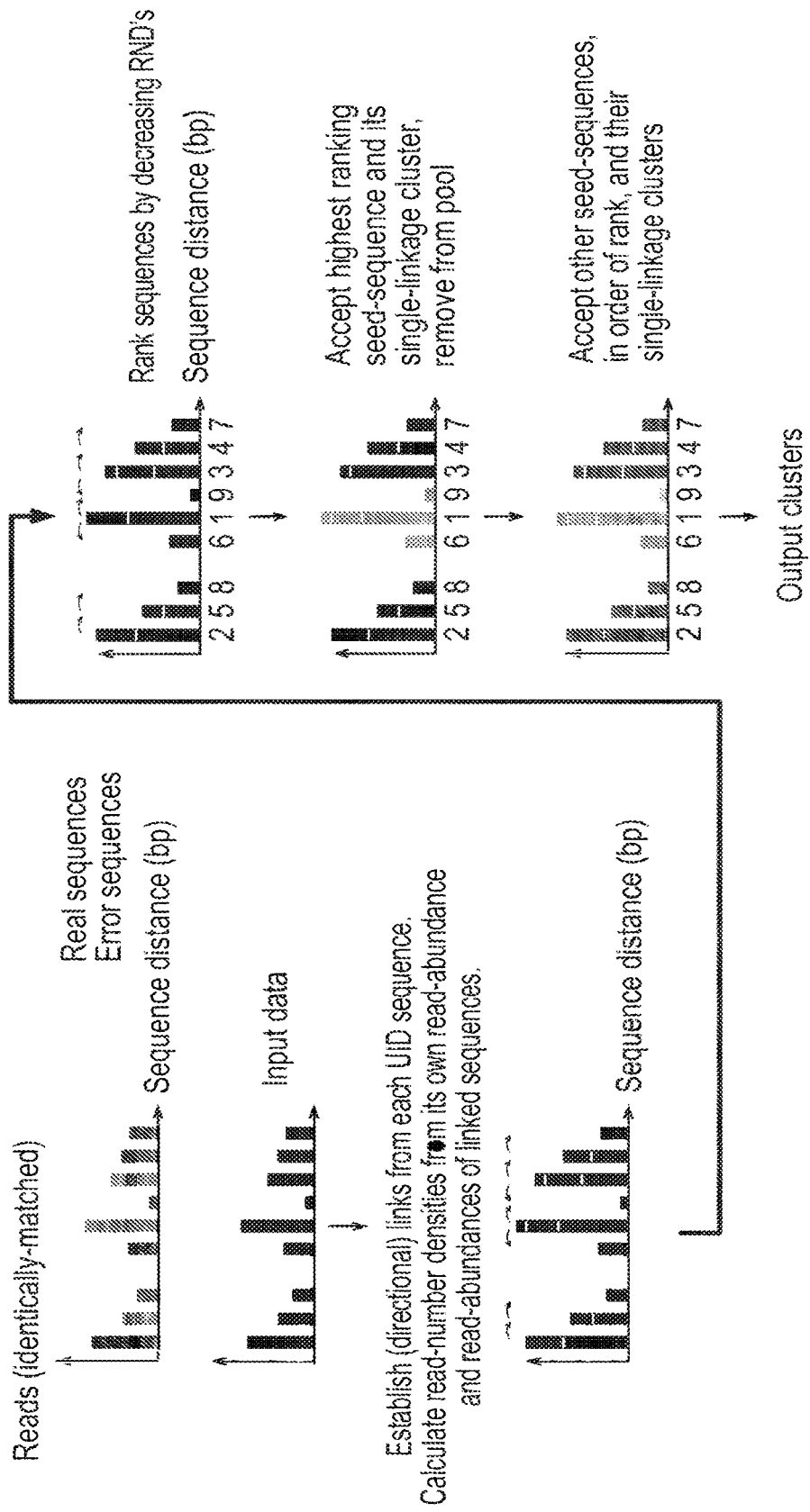
FIG. 8 depicts an EASL clustering iteration.
Figure 9:
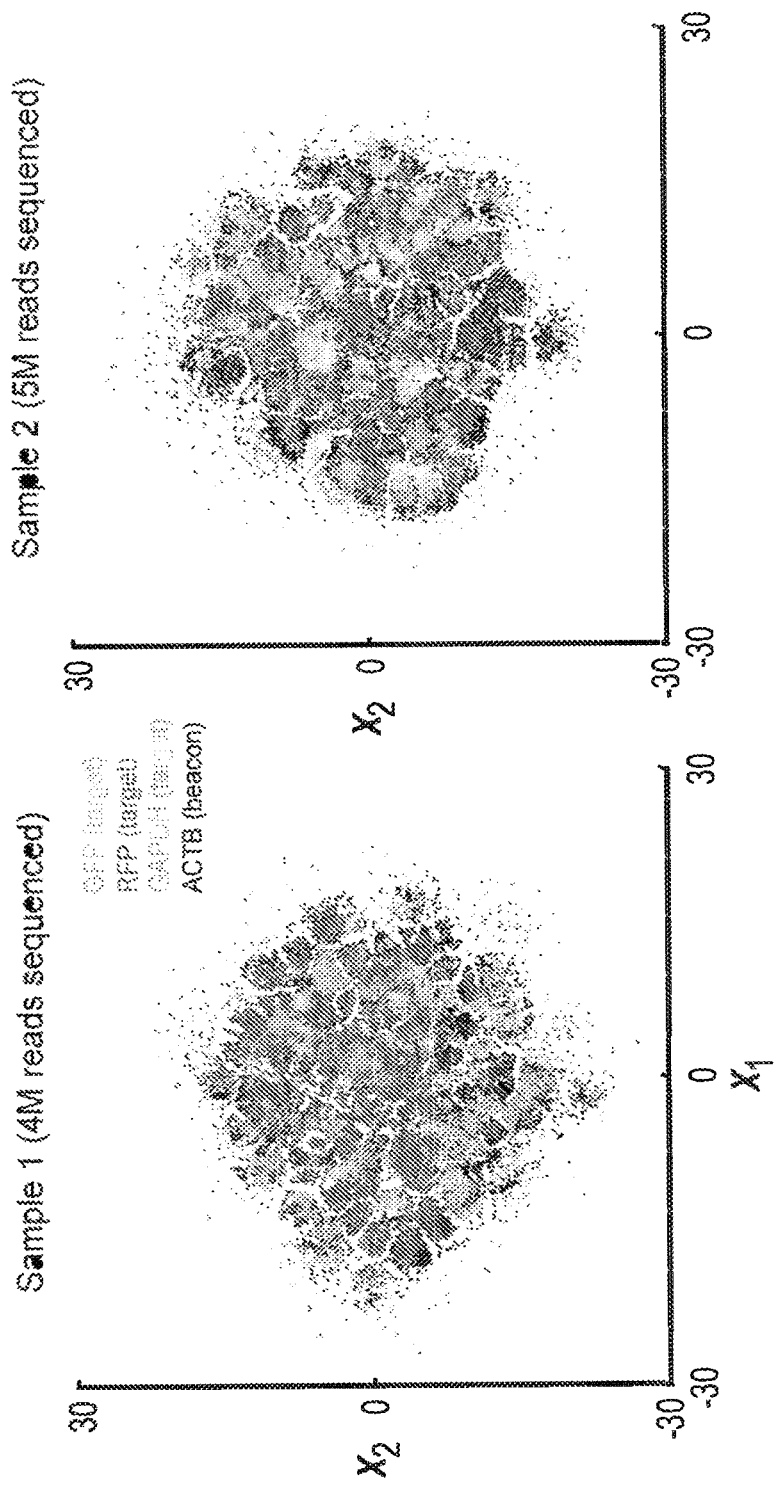
FIG. 9 depicts inferred positions of transcript sequences from a Beacon-Target DNA microscopy experiment.

Each sequencing-read is comprised of three types of segments: "primers", "UMI's" or "UEI's", and "amplicons". The form this takes on as a paired-end read is illustrated in FIG. 3. Beacon UMI's, target UMI's, and UEI's are separated from each other into distinct analyses. These are analyzed and grouped in order to eliminate sequencing and PCR error using an algorithm, here called extended abundance single-linkage (EASL) clustering, which is analogous to the Watershed Algorithm for image processing (FIG. 8).

The EASL clustering algorithm is designed for rapid identification of UMI/UEI sequence-clusters based on single-mismatch alignments alone. EASL presupposes that a sequence is more likely to occur in the dataset the nearer it is to its correct form.

EASL initiates by grouping every UMI/UEI (of the same type and within the same data-set) by perfect identity, and read-abundance is assigned to each UMI/UEI sequence by the number of reads identically grouped in this manner. Each pair of UMI's or UEI's (of the same type and within the same data-set) is compared in an un-gapped alignment. UMI/UEI i (directionally) links to UMI/UEI j if and only if the read-abundance of UMI/UEI i is greater than or equal to the read-abundance of UMI/UEI j. In order to accelerate this process local similar hashing may be used (FIG. 8).

Read number densities, or RND's, are calculated for each UMI/UEI sequence by summing read-abundances belonging both to the sequence itself and all sequences (of equal or lower abundance) it links to. The UMI/UEI with the largest RND initiates clustering as the first cluster-seed. All UMI/UEI's to which this seed links by the aforementioned criterion are accepted into its cluster, all UMI/UEI's to which these newly accepted UMI/UEI's link are accepted as well, and so on. In this way, single-linkage clusters are formed in which the linkages themselves are not always bidirectional.

Once no further assignments can be made to the first cluster, the algorithm proceeds to the UMI/UEI with the next largest RND that has not already been accepted into a cluster. The same cluster-assembly proceeds among all un-assigned UMI's or UEI's. When no un-assigned UMI/UEI remains, the algorithm terminates.

The iteration of the EASL algorithm is illustrated in FIG. 8.

The number of N's to use in a UMI/UEI will depend on the expected diversity of molecules and/or events being tagged. Assuming an upper-bound for this diversity is known, the question reduces to the so-called "birthday-problem". Given a UMI/UEI length, the probability that two randomly-drawn UMI's or UEI's will match (assuming uniform base-distributions) is $P_0(l)=4^{-l}$.

Similarly, the probability that there will be another UMI/UEI within 1 bp is $$p_{\leq 1}(l) = \frac{1+3l}{4^l}$$

The probability that no two UMI's or UEI's out of N will overlap in this way is Prob(0 overlap)=$(1-P_{\leq 1}(l))(1-2P_{\leq 1}(l))\ldots(1-(N-1)P_{\leq 1}(l))$ If $N_{crit}(l)$ is defined through the relation $\frac{1}{2}=(1-P_{\leq 1}(l))(1-2P_{\leq 1}(l))\ldots(1-(N_{crit}(l)-1)P_{\leq 1}(l))$ then $N_{crit}(l)$ is the maximum diversity of templates beyond which it becomes likely that at least 1 pair of UMI/UEI sequences will be within 1 bp of one another. For l=21, the number currently used in experiments, $N_{crit} \approx 3 \times 10^5$. However, this is only for single target gene sequences. For a set of sequence frequencies $\{p_1, p_2, \ldots, p_S\}$ (normalized to sum to one) of S distinct sequence-types labeled by UMI's, the probability that two randomly selected sequences will be the same is $\lambda = \Sigma_i p_i^2$. This measure, also known as Simpson's diversity index, affects the calculation above by multiplying $P_{\leq 1}$. The more diverse and distributed the population of sequences, the smaller the product $\lambda P_{\leq 1}$ and the larger the value of $N_{crit}(l)$.

It should moreover be noted that the picture is far simpler for UEI's than for UMI's. Because a UEI brings together exactly two UMI's, two UEI's that are grouped together will get one vote as to which pair of UMI's they associate (assigned via read-plurality). Therefore, the less abundant indistinguishable UEI will simply be ignored. From here it can be determined that the UEI diversity is far closer to the upper limit of that which is physically possible ($4^l$, or in the case of oligos in TABLE 2, where the UEI's have 20 N-nucleotides, ~$10^{12}$) without substantial problems.

Verifying the sufficiency of UMI/UEI length boils down to comparing those found in different experiments (something that also helps in tracking cross-contamination). Once abundance filters ($\geq 2$ reads) and composition filters (75% maximum majority for a single base) are applied, little if any overlap has been observed in any of the runs analyzed.

Consider the diffusion profile of products of a single UMI with index i, centered at position $x_i$, during an amplification experiment. This can be written $$c_i(\vec{x}) \propto t^{-d/2} e^{-\|\vec{x}-\vec{x}_i\|^2/4dDt+At} \quad (1)$$

where d is the dimensionality (of space), D is the diffusion constant, and $A = \log 2/\Delta t$ where $\Delta t$ is the time-scale of a PCR cycle. The rate of crosslink product formation between UMI's i and j with the same diffusion constant will then be the volume-integral $$\phi_{ij}(t) \propto \int_{\vec{x}} c_i(\vec{x}_i, \vec{x}, t) c_j(\vec{x}_j, \vec{x}, t) dV \quad (2)$$

$$\propto t^{-d} e^{-\|\vec{x}_i-x_j\|^2/8dDt+2At} \int_{\vec{x}} e^{-\|x-(\vec{x}_i+\vec{x}_j)/2\|^2/2dDt} dV \quad (3)$$

$$\propto t^{-d/2} e^{-\|\vec{x}_i-x_j\|^2/8dDt+2At} \quad (4)$$

This rate equation provides the foundation to build maximum likelihood estimates (MLE) of positions, given the observed rates of UEI formation—which is really the summation of rates, $\Sigma_{t=1}^{t_{max}} \phi_{ij}(t)$ over the duration of the experiment. Here an MLE solution was developed, which is time-independent.

For the time-independent MLE, the approximation is considered where, in some units of space $\vec{x}$, $\Sigma_{t=1}^{t_{max}} \phi_{ij}(t) \rightarrow e^{-\|\vec{x}_i-\vec{x}_j\|^2+A_i+A_j} \equiv w_{ij}$. The amplification constants $A_i$ and $A_j$ may be interpreted as free parameters belonging to each UMI that account for discrepancies both in amplification efficiency and other sources of over- and under-sampling.

Applicants can use the normalized frequency of concatenation between UMI's i and j, $w_{ij}/w$. (where each "." represents summation over an index) to calculate the likelihood of a solution wherein $n_{ij}$ unique UEI's occur between beacon UMI i and target UMI j:

$$\text{Prob}(\{\vec{x}_i\}, \{\vec{x}_j\} \mid \{n_{ij}\}) \propto \prod_{i,j} \left(\frac{w_{ij}}{w_{..}}\right)^{n_{ij}} \quad (5)$$

The gradient is now calculated for the log-probability from Equation (5)

$$\mathcal{L} = \sum_{ij} n_{ij} \log w_{ij} - n_{..} \log w_{..}$$

and its gradient with respect to some attribute (either position or amplification constant) or a UMI k:

$$\partial_k \mathcal{L} = \sum_j \frac{n_{kj}}{w_{kj}} \partial_k w_{kj} - \frac{n_{..}}{w_{..}} \partial_k w_k.$$

In the above, the first term can be calculated quickly, because of the sparse nature of the matrix $n_{ij}$. The second term requires special treatment, because explicit evaluation would otherwise require an $O(N_{beacon} \times N_{target})$ calculation at every MLE-maximization iteration. The Fast Gauss Transform is therefore used [Greengard and Strain. The fast Gauss Transform, SIAM Journal on Scientific and Statistical Computing, 1991].

Fixation of cells or tissue may involve the use of cross-linking agents, such as formaldehyde, and may involve embedding cells or tissue in a paraffin wax or polyacrylamide support matrix (Chung K, et al. Nature. 2013 May 16; 497(7449): 322-7).

Amplification may involve thermocycling or isothermal amplification (such as through the methods RPA or LAMP). Concatenation may involve overlap-extension PCR or use of ligase, recombinase, or transposase to associate multiple amplification products with each other. Concatenation can further comprise an additional incorporation of a unique UEI labeling step. In certain embodiments, at least one UMI is a completely random or computationally designed 10 to 50 mer between a gene-specific and adapter region of a primer used for reverse transcription. The method may further comprise concatenation amplification products of in situ amplification of template nucleic acid sequences and/or of overlap extension products.

For purpose of this invention, amplification means any method employing a primer and a polymerase capable of replicating a target sequence with art recognized standards of fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dyes suitable for this application include SYBR™ green, SYBR™ blue, DAPI, propidium iodine, Hoeste, SYBR™ gold, ethidium bromide, acridines, proflavine, acridine orange, acriflavine, fluorocoumarin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. Such methods utilize fluorescent, target-specific probes (e.g., TaqMan® probes) resulting in increased specificity and sensitivity. Methods for performing probe-based quantitative amplification are well established in the art and are taught, for example, in U.S. Pat. No. 5,210,015.

Sequencing may be performed on any high-throughput platform with read-length (either single- or paired-end) sufficient to cover both template molecule identifiers (UMI's) and concatenation event identifiers (UEI's). Methods of sequencing oligonucleotides and nucleic acids are well known in the art (see, e.g., WO93/23564, WO98/28440 and WO98/13523; U.S. Pat. Nos. 5,525,464; 5,202,231; 5,695,940; 4,971,903; 5,902,723; 5,795,782; 5,547,839 and 5,403,708; Sanger et al., Proc. Natl. Acad. Sci. USA 74:5463 (1977); Drmanac et al., Genomics 4:114 (1989); Koster et al., Nature Biotechnology 14:1123 (1996); Hyman, Anal. Biochem. 174:423 (1988); Rosenthal, International Patent Application Publication 761107 (1989); Metzker et al., Nucl. Acids Res. 22:4259 (1994); Jones, Biotechniques 22:938 (1997); Ronaghi et al., Anal. Biochem. 242:84 (1996); Ronaghi et al., Science 281:363 (1998); Nyren et al., Anal. Biochem. 151:504 (1985); Canard and Arzumanov, Gene 11:1 (1994); Dyatkina and Arzumanov, Nucleic Acids Symp Ser 18:117 (1987); Johnson et al., Anal. Biochem. 136:192 (1984); and Elgen and Rigler, Proc. Natl. Acad. Sci. USA 91(13):5740 (1994), all of which are expressly incorporated by reference).

The present invention may be applied to (1) single-cell transcriptomics: cDNA synthesized from mRNA is barcoded and concatenated during in situ amplification, (2) single-cell proteomics: cDNA or DNA synthesized from RNA- or DNA-tagged antibodies of one or multiple specificities maps the abundance and distributions of different protein-antigens and (3) whole-tissue transcriptomic/proteomic mapping (DNA microscopy): using the frequency of cross-contamination between cells to determine their physical proximity, and via applications (1) single-cell transcriptomics and (2) single-cell proteomics, determining the global spatial distribution of mRNA, protein, or other biomolecules in a biological sample. This may be used, for example, to screen for anti-cancer/pathogen immunoglobulins (by analyzing co-localization of B-cells and T-cells within affected tissue) for immunotherapy.

TABLE 1

Techniques for overlap-extension suppression during library preparation.

| Technique | Description |
| --- | --- |
| Blocking oligos | 3'-capped oligos complementary to both overlap-extension ends (10 and 10' in FIG. 3) added at high concentration during NGS library preparation phase (FIG. 3, vi). See Turchaninova MA et al. Eur J Immunol. 2013 Sep; 43(9): 2507-15. |
| T7-exo + Exo-I treatment | At least 3 phosphorothioate nucleotides are added to each 5' end of primers (5) and (8) for use during in situ amplification. After elution, products are digested with both T7-exonuclease and exonuclease I in order to eliminate monomeric products. |
| Biotin pulldown | Biotin is added to either primer (5) or primer (8) for use during in situ amplification. After elution, products are pulled down with streptavidin beads, in order eliminate either one of the monomeric products. |

TABLE 2

List of primer-sequences for Beacon-Target embodiment. The number of random nucleotides in primers beginning with are determined by either the expected diversity of template cDNA molecules being amplified (for UMI diversity, in the case of (5)-(2)-X and (3)-(2)-X) or the expected diversity required to uniquely identify overlap-extension events (for UEI diversity, in the case of (10)-(2)-X and (10')-(2)-X). "XXXXXXXX" for primer (12)-(5) represents the sample barcode (which is non-random), and is represented by NNNNNNNN in the attached Sequence Listing

| Stage used | Alias | Sequence |
| --- | --- | --- |
| Reverse transcription SEQ. ID. No. 1 | (5)-(2)-(4)-GAPDH | CGTGTGCTCTTCCGATCTTNNNNNNNATNNNNNN NATNNNNNNNNTTACTCCTTGGAGGCCATGT |
| Reverse transcription SEQ. ID. No. 2 | (5)-(2)-(4)-GFP | CGTGTGCTCTTCCGATCTTNNNNNNNATNNNNNN NATNNNNNNNNTCTTGAAGTTCACCTTGATGC |
| Reverse transcription SEQ. ID. No. 3 | (5)-(2)-(4)-RFP | CGTGTGCTCTTCCGATCTTNNNNNNNATNNNNNN NATNNNNNNNNCCATGGTCTTCTTCTGCATT |
| Reverse transcription SEQ. ID. No. 4 | (3)-(2)-(1)-ACTB | GAGGTGTCCTAAACTTACGCNNNNNNNNATNNNNN NNATNNNNNNNNTAGATCGGAAGAGCGTCGAGAGA AGTGGGGTGGCTTTT |
| 2nd strand-synthesis/linear amp SEQ. ID. No. 5 | (9sh)-(7(-))-GAPDH | TGGTCTCAACATATCGCATCCTGGGCTACACTGA GCACCAGG |
| 2nd strand-synthesis/linear amp SEQ. ID. No. 6 | (9sh)-(7(-))-GFP | TGGTCTCAACATATCGCACCATCTTCTTCAAGGA CGACGGCAAC |
| 2nd strand-synthesis/linear amp SEQ. ID. No. 7 | (9sh)-(7(-))-RFP | TGGTCTCAACATATCGCAGTTCATGTACGGCTCC AAGGCCTAC |
| 2nd strand-synthesis/linear amp SEQ. ID. No. 8 | (8sh)-(6(-))-ACTB | TGGCTTCAAATTCACGCAAACTGGAACGGTGAAG GTGACAGCAG |
| OE-PCR SEQ. ID. No. 9 | (5) | GTTCAGACGTGTGCTCTTCCGATCT |
| OE-PCR SEQ. ID. No. 10 | (8) | ATGAGTGGCTTCAAATTCACGC |
| OE-PCR SEQ. ID. No. 11 | (10')-(2)-(9) | /5Acryd/GGCGCGCCATGGGAATAANNNNNNATN NNNNTGGAGTGGTCTCAACATATCGC |
| OE-PCR SEQ. ID. No. 12 | (10)-(2)-(3) | /5Acryd/TATTCCCATGGCGCGCCANNNNNNATN NNNNTTGAGGTGTCCTAAACTTACGC |
| Re-amplification/library prep SEQ. ID. No. 13 | (1'(long)) | AATGATACGGCGACCACCGAGATCTACACTCTTT CCCTACACGACGCTCTTCCGATCT |
| Re-amplification/library prep SEQ. ID. No. 14 | (12)-(5) | CAAGCAGAAGACGGCATACGAGATNNNNNNNNGT GACTGGAGTTCAGACGTGTGCTCTTCCGATCT |

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. % homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p 387). Examples of other software than may perform sequence comparisons include, but are not limited to, the BLAST package (see Ausubel et al., 1999 Short Protocols in Molecular Biology, 4th Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999174(2): 247-50; FEMS Microbiol Lett. 1999177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphorimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., $^{32}$P, $^{14}$C, $^{125}$I, $^{3}$H, and $^{131}$I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'-disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcourmarin (Coumarin 151); cyanine dyes; cyanosine; 4',6-diamidino-2-phenylindole (DAPI); 5'5"-dibromopyrogallol-sulfonaphthalene (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron.TM. Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red®); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolla Blue™; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., international patent application serial no. PCT/US2013/61182 filed Sep. 23, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the non-nucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, a detectable oligonucleotide tag comprises one or more non-oligonucleotide detectable moieties. Examples of detectable moieties include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties are quantum dots. Methods for detecting such moieties are described herein and/or are known in the art.

Thus, detectable oligonucleotide tags may be, but are not limited to, oligonucleotides comprising unique nucleotide sequences, oligonucleotides comprising detectable moieties, and oligonucleotides comprising both unique nucleotide sequences and detectable moieties.

A unique nucleotide sequence may be a nucleotide sequence that is different (and thus distinguishable) from the sequence of each detectable oligonucleotide tag in a plurality of detectable oligonucleotide tags. A unique nucleotide sequence may also be a nucleotide sequence that is different (and thus distinguishable) from the sequence of each detectable oligonucleotide tag in a first plurality of detectable oligonucleotide tags but identical to the sequence of at least one detectable oligonucleotide tag in a second plurality of detectable oligonucleotide tags. A unique sequence may differ from other sequences by multiple bases (or base pairs). The multiple bases may be contiguous or non-contiguous. Methods for obtaining nucleotide sequences (e.g., sequencing methods) are described herein and/or are known in the art.

In some embodiments, detectable oligonucleotide tags comprise one or more of a ligation sequence, a priming sequence, a capture sequence, and a unique sequence (optionally referred to herein as an index sequence). A ligation sequence is a sequence complementary to a second nucleotide sequence which allows for ligation of the detectable oligonucleotide tag to another entity comprising the second nucleotide sequence, e.g., another detectable oligonucleotide tag or an oligonucleotide adapter. A priming sequence is a sequence complementary to a primer, e.g., an oligonucleotide primer used for an amplification reaction such as but not limited to PCR. A capture sequence is a sequence capable of being bound by a capture entity. A capture entity may be an oligonucleotide comprising a nucleotide sequence complementary to a capture sequence, e.g. a second detectable oligonucleotide tag. A capture entity may also be any other entity capable of binding to the capture sequence, e.g. an antibody or peptide. An index sequence is a sequence comprising a unique nucleotide sequence and/or a detectable moiety as described above.

"Complementary" is a term which is used to indicate a sufficient degree of complementarity between two nucleotide sequences such that stable and specific binding occurs between one and preferably more bases (or nucleotides, as the terms are used interchangeably herein) of the two sequences. For example, if a nucleotide in a first nucleotide sequence is capable of hydrogen bonding with a nucleotide in second nucleotide sequence, then the bases are considered to be complementary to each other. Complete (i.e., 100%) complementarity between a first nucleotide sequence and a second nucleotide is preferable, but not required for ligation, priming, or capture sequences.

The present invention also relates to a computer system involved in carrying out the methods of the invention relating to both computations and sequencing.

A computer system (or digital device) may be used to receive, transmit, display and/or store results, analyze the results, and/or produce a report of the results and analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers).

In some embodiments, the computer system comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

A machine readable medium comprising computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device comprising a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for recording cellular co-localization and/or spatial distributions of nucleic acid sequences and/or biomolecules tagged with a nucleic acid in non-dissociated cells or fixed tissue comprising:
   (a) labeling template nucleic acid sequences in non-dissociated cells or fixed tissues with unique molecular identifiers (UIDs), wherein the labeling comprises adding at least one α-UID to each template nucleic acid, thereby generating uniquely labeled template nucleic acids;
   (b) amplifying the labeled template nucleic acids using in situ amplification, wherein the amplification reaction also comprises concatenating individual amplified labeled template nucleic acids together such that each concatenation event results in incorporation of at least one unique β-UID, wherein the frequency of concatenation events between amplified labeled template nucleic acids is a function of the proximity of each individual labeled template nucleic acid to another labeled template nucleic acid; and
   (c) generating a spatially resolved physical mapping of the non-dissociated cells or fixed tissue by isolation and sequencing of the uniquely labeled concatenation events from (b).

2. The method of claim 1, wherein the nucleic acid in the non-dissociated cells or fixed tissue is DNA.

3. The method of claim 2, wherein the DNA is complementary DNA (cDNA).

4. The method of claim 1, wherein the nucleic acid in the non-dissociated cells or fixed tissue is RNA.

5. The method of claim 1, wherein cells of the non-cells or fixed tissue are fixed and permeabilized.

6. The method of claim 1, wherein the at least one α-UID is a completely random or computationally designed 10 to 50 mer between a gene-specific and adapter region of a primer used for reverse transcription.

7. The method of claim 6, wherein the at least one α-UID comprises DNA or RNA.

8. The method of claim 1, wherein the concatenation further comprises an additional incorporation of a unique β-UID step.

9. The method of claim 1, wherein the amplification comprises thermocycling.

10. The method of claim 1, wherein the amplification occurs in solution, or on a solid support.

11. The method of claim 10, wherein the solid support comprises a glass slide, glass beads, PDMS, or a combination thereof.

12. The method of claim 1, wherein the concatenation comprises overlap-extension polymerase chain reaction.

13. The method of claim 1, wherein the concatenation comprises associating multiple amplification products with a ligase, recombinase, or transposase.

14. The method of claim 1, further comprising detection of the amplified nucleic acid sequences.

15. The method of claim 14, wherein the amplified nucleic acid sequences are detected using a fluorescent DNA-binding agent or sequence-specific probe.

16. The method of claim 1, wherein the non-dissociated cells or fixed tissue comprises tumor tissue, lymphatic tissue, or neural tissue.

17. The method of claim 1, wherein the β-UID comprises at least 10 random bases.

18. The method of claim 1, wherein the amplification comprises isothermal amplification.

19. The method of claim 1, wherein the amplification occurs in a hydrogel.

* * * * *

UNITED STATES PATENT AND TRADEMARK OFFICE
CERTIFICATE OF CORRECTION

PATENT NO. : 11,339,390 B2
APPLICATION NO. : 15/554627
DATED : May 24, 2022
INVENTOR(S) : Feng Zhang, Joshua Asher Weinstein and Aviv Regev It is certified that error appears in the above-identified patent and that said Letters Patent is hereby corrected as shown below:

In the Specification

Column No. 7, Line No. 57, "(400" should be -- (400 µM), --
Column No. 9, Line No. 30, "UMI/UEI" should be -- UMI/UEI i --
Column No. 9, Line No. 57, "length," should be -- - length ℓ --
Column No. 10, Line No. 64, "wij/w." should be -- wij/w.. --
Column No. 13-14 (Table 2), Line No. 20 (approx.), "No.6" should be -- No. 6 --
Column No. 17, Line No. 56, "1999174(2):" should be -- 1999 174(2): --
Column No. 17, Line No. 57, "1999177(1 ):" should be -- 1999 177(1): --

Signed and Sealed this
Eighteenth Day of October, 2022

Katherine Kelly Vidal
*Director of the United States Patent and Trademark Office*

SEQUENCE LISTING

```
<160> NUMBER OF SEQ ID NOS: 23

<210> SEQ ID NO 1
<211> LENGTH: 64
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (20)..(26)
<223> OTHER INFORMATION: n is a, c, g, or t
<220> FEATURE:
<221> NAME/KEY: misc_feature
<222> LOCATION: (29)..(35)
<223> OTHER INFORMATION: n is a, c, g, or t
<220> FEATURE:
<221> NAME/KEY: misc_feature
<222> LOCATION: (38)..(44)
<223> OTHER INFORMATION: n is a, c, g, or t

<400> SEQUENCE: 1
cgtgtgctct tccgatcttn nnnnnnatnn nnnnnatnnn nnnnttactc cttggaggcc    60
atgt                                                                64

<210> SEQ ID NO 2
<211> LENGTH: 65
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (20)..(26)
<223> OTHER INFORMATION: n is a, c, g, or t
<220> FEATURE:
<221> NAME/KEY: misc_feature
<222> LOCATION: (29)..(35)
<223> OTHER INFORMATION: n is a, c, g, or t
<220> FEATURE:
<221> NAME/KEY: misc_feature
<222> LOCATION: (38)..(44)
<223> OTHER INFORMATION: n is a, c, g, or t
```

<400> SEQUENCE: 2
cgtgtgctct tccgatcttn nnnnnnatnn nnnnnatnnn nnnntcttga agttcacctt    60
gatgc    65

<210> SEQ ID NO 3
<211> LENGTH: 64
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (20)..(26)
<223> OTHER INFORMATION: n is a, c, g, or t
<220> FEATURE:
<221> NAME/KEY: misc_feature
<222> LOCATION: (29)..(35)
<223> OTHER INFORMATION: n is a, c, g, or t
<220> FEATURE:
<221> NAME/KEY: misc_feature
<222> LOCATION: (38)..(44)
<223> OTHER INFORMATION: n is a, c, g, or t

<400> SEQUENCE: 3
cgtgtgctct tccgatcttn nnnnnnatnn nnnnnatnnn nnnnccatgg tcttcttctg    60
catt    64

<210> SEQ ID NO 4
<211> LENGTH: 83
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (21)..(27)
<223> OTHER INFORMATION: n is a, c, g, or t
<220> FEATURE:
<221> NAME/KEY: misc_feature
<222> LOCATION: (30)..(36)
<223> OTHER INFORMATION: n is a, c, g, or t
<220> FEATURE:
<221> NAME/KEY: misc_feature
<222> LOCATION: (39)..(45)
<223> OTHER INFORMATION: n is a, c, g, or t

<400> SEQUENCE: 4
gaggtgtcct aaacttacgc nnnnnnnatn nnnnnnatnn nnnntagat cggaagagcg    60 tcgagagaag tggggtggct ttt    83

<210> SEQ ID NO 5
<211> LENGTH: 42
<212> TYPE: DNA
<213> ORGANISM: Artificial Sequence
<220> FEATURE:
<223> OTHER INFORMATION: Artificial primer

<400> SEQUENCE: 5
tggtctcaac atatcgcatc ctgggctaca ctgagcacca gg    42

<210> SEQ ID NO 6
<211> LENGTH: 44
<212> TYPE: DNA
<213> ORGANISM: Artificial Sequence
<220> FEATURE:
<223> OTHER INFORMATION: Synthetic primer

<400> SEQUENCE: 6
tggtctcaac atatcgcacc atcttcttca aggacgacgg caac        44

<210> SEQ ID NO 7
<211> LENGTH: 43
<212> TYPE: DNA
<213> ORGANISM: Artificial Sequence
<220> FEATURE:
<223> OTHER INFORMATION: Synthetic primer

<400> SEQUENCE: 7
tggtctcaac atatcgcagt tcatgtacgg ctccaaggcc tac         43

<210> SEQ ID NO 8
<211> LENGTH: 44
<212> TYPE: DNA
<213> ORGANISM: Artificial Sequence
<220> FEATURE:
<223> OTHER INFORMATION: Synthetic primer

<400> SEQUENCE: 8
tggcttcaaa ttcacgcaaa ctggaacggt gaaggtgaca gcag        44

<210> SEQ ID NO 9
<211> LENGTH: 25
<212> TYPE: DNA
<213> ORGANISM: Artificial Sequence
<220> FEATURE:
<223> OTHER INFORMATION: Synthetic primer

<400> SEQUENCE: 9
gttcagacgt gtgctcttcc gatct                            25

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
atgagtggct tcaaattcac gc                               22

<210> SEQ ID NO 11
<211> LENGTH: 52
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Guanine residue at position 1 bears /5Acryd/
      attachment
<220> FEATURE:
<221> NAME/KEY: misc_feature
<222> LOCATION: (19)..(23)
<223> OTHER INFORMATION: n is a, c, g, or t
<220> FEATURE:
<221> NAME/KEY: misc_feature
<222> LOCATION: (26)..(30)
<223> OTHER INFORMATION: n is a, c, g, or t

<400> SEQUENCE: 11
ggcgcgccat gggaataann nnnatnnnnn tggagtggtc tcaacatatc gc    52

<210> SEQ ID NO 12

```
<211> LENGTH: 52
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Thymine residue at position 1 bears /5Acryd/
      attachment
<220> FEATURE:
<221> NAME/KEY: misc_feature
<222> LOCATION: (19)..(23)
<223> OTHER INFORMATION: n is a, c, g, or t
<220> FEATURE:
<221> NAME/KEY: misc_feature
<222> LOCATION: (26)..(30)
<223> OTHER INFORMATION: n is a, c, g, or t

<400> SEQUENCE: 12
tattcccatg gcgcgccann nnnatnnnnn ttgaggtgtc ctaaacttac gc          52

<210> SEQ ID NO 13
<211> LENGTH: 58
<212> TYPE: DNA
<213> ORGANISM: Artificial Sequence
<220> FEATURE:
<223> OTHER INFORMATION: Synthetic primer

<400> SEQUENCE: 13
aatgatacgg cgaccaccga gatctacact ctttccctac acgacgctct tccgatct    58

<210> SEQ ID NO 14
<211> LENGTH: 66
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (25)..(32)
<223> OTHER INFORMATION: Represents the sample barcode (which is
      non-random)

<400> SEQUENCE: 14
caagcagaag acggcatacg agatnnnnnn nngtgactgg agttcagacg tgtgctcttc  60
cgatct                                                            66

<210> SEQ ID NO 15
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 15
tttttttttt tattcccatg gcgcgcca                                    28

<210> SEQ ID NO 16
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 16
tttttttttt ggcgcgccat gggaataa                                    28
```

<210> SEQ ID NO 17
<211> LENGTH: 28
<212> TYPE: DNA
<213> ORGANISM: Artificial Sequence
<220> FEATURE:
<223> OTHER INFORMATION: Synthetic primer

<400> SEQUENCE: 17
cccacttctc tcgacgctct tccgatct                                          28

<210> SEQ ID NO 18
<211> LENGTH: 143
<212> TYPE: DNA
<213> ORGANISM: Artificial Sequence
<220> FEATURE:
<223> OTHER INFORMATION: Synthetic

<400> SEQUENCE: 18
taaaagccac cccacttctc tactaaatat ctaccgattc ccttgcgtaa gtttaggaca        60
cctcaatgca cattaagctg gcgcgccatg ggaataaaag atataaaaat ggagtggtct      120
caacatatcg catcctgggc tac                                              143

<210> SEQ ID NO 19
<211> LENGTH: 143
<212> TYPE: DNA
<213> ORGANISM: Artificial Sequence
<220> FEATURE:
<223> OTHER INFORMATION: Synthetic

<400> SEQUENCE: 19
ccccgaccgt aacgggagtt gctggtgaaa cagttcgagt aaaggaccat actgttgctt        60
aaaccgatgt cgttgtccca ccacctggag taccgggtgt accggaggtt cctcattgta      120
ggcgtactcg aggtaggtcc aat                                              143

<210> SEQ ID NO 20
<211> LENGTH: 142
<212> TYPE: DNA
<213> ORGANISM: Artificial Sequence
<220> FEATURE:
<223> OTHER INFORMATION: Synthetic

<400> SEQUENCE: 20
gtggcttcaa attcacgcat cctgggctac actgagcacc aggtggtctc ctctgacttc        60
aacagcgaca cccactcctc cacctttgac gctggggctg gcattgccct caacgaccac      120
tttgtcaagc tcatttcctg gt                                               142

<210> SEQ ID NO 21
<211> LENGTH: 142
<212> TYPE: DNA
<213> ORGANISM: Artificial Sequence
<220> FEATURE:
<223> OTHER INFORMATION: Synthetic

<400> SEQUENCE: 21
accgggtgta ccggaggttc ctcatttggg tggtaggtaa gataagtaca tcgcattcaa        60
atcctgtgga gttagaagac ccacctacga caaccgcgcg gtacccttat actagctact      120
tgcgtctcta tactcaccga at                                               142

<210> SEQ ID NO 22
<211> LENGTH: 142
<212> TYPE: DNA

```
<213> ORGANISM: Artificial Sequence
<220> FEATURE:
<223> OTHER INFORMATION: Synthetic

<400> SEQUENCE: 22
ggtgtcctaa acttacgcaa gatagattaa cactatttct gacttactcc ttggaggcca      60
tgtgggccat gaggtccacc accctgttgc tgtagccaaa ttcgttgtca taccaggaaa     120
tgagcttgac aaagtggtcg tt                                              142

<210> SEQ ID NO 23
<211> LENGTH: 142
<212> TYPE: DNA
<213> ORGANISM: Artificial Sequence
<220> FEATURE:
<223> OTHER INFORMATION: Synthetic

<400> SEQUENCE: 23
cagcgacaac ttcagtctcc tctggtggac cacgagtcac atcgggtcct acgcacttaa      60
acttcggtga gtatagagac ttgattaatc ataataaggg taccgcgcgg tcaccctaca     120
gcggtcttct aactccacag gt                                              142
```